United States Patent [19]

Koshar et al.

[11] 4,054,596
[45] Oct. 18, 1977

[54] CARBOXY AND CARBOHYDROCARBYLOXY-SUBSTITUTED 1,1-BIS(PERFLUOROALKYLSULFONYL)-PROPANES

[75] Inventors: Robert J. Koshar, Mahtomedi; Loren L. Barber, Jr., Woodbury, both of Minn.

[73] Assignee: Minnesota Mining and Manufacturing Company, St. Paul, Minn.

[21] Appl. No.: 556,494

[22] Filed: Mar. 7, 1975

[51] Int. Cl.² .................. C07C 147/02; C07C 147/06
[52] U.S. Cl. .......................... 560/150; 260/47 EP; 260/326 H; 260/465.7; 260/537 S; 260/590 D; 260/592; 260/593 H; 260/607 A; 560/145

[58] Field of Search ............ 260/481 R, 537 S, 479S

[56] References Cited

U.S. PATENT DOCUMENTS

| | | | |
|---|---|---|---|
| 3,758,531 | 9/1973 | Kashar | 260/481 R |
| 3,794,687 | 2/1974 | Koshar | 260/481 R |
| 3,940,435 | 2/1976 | Hiestand | 260/481 R |

*Primary Examiner*—Vivian Garner
*Attorney, Agent, or Firm*—Cruzan Alexander; Donald M. Sell; Temple Clayton

[57] ABSTRACT

1,1-Bis(perfluoroalkylsulfonyl)propanes substituted in the three position by two to three electron-withdrawing groups, particularly perfluoroalkylsulfonyl, carboxyl, carboalkoxy or cyano are catalysts for the polymerization of aromatic epoxy resins.

3 Claims, No Drawings

CARBOXY AND CARBOHYDROCARBYLOXY-SUBSTITUTED 1,1-BIS(PERFLUOROALKYLSULFONYL)PROPANES

This invention relates to a new class of fluorinecontaining acidic compounds and more particularly to substituted 1,1-bis(perfluoroalkylsulfonyl)propanes. The invention also relates to metallic and organic salts of the said acidic materials. These novel compounds find use as catalysts for polymerization of epoxy compositions, particularly aromatic glycidyl ethers, the salts being generally useful as latent catalysts providing the acidic materials on heating.

Various bis(highly fluorinated alkyl sulfonyl)methane compounds have been used as catalysts for curing epoxy prepolymers. Usually elevated temperatures are required for rapid complete curing of aromatic epoxy resin prepolymers such as the bis-glycidyl ether of bisphenol A. Comparative results using such a fluorinated disulfonylmethane are tabulated for numerous types of epoxy resin prepolymers in Table I of Allen et al., U.S. Pat. No. 3,632,843 which show that when catalyzed by bis(perfluoromethylsulfonyl)methane, Epon 828 (a commercial bisphenol A bis-glycidylether) remains as a viscous unpolymerized liquid for at least 15 minutes at room temperature but cures to a hard solid in 5 minutes at 80° C. Other examples also show that heating is needed for this combination. Other bis(perfluoroalkylsulfonyl)methanes having additional substituents are described in U.S. Pats. Nos. 3,758,592 and 3,794,687.

Bis (perfluoroalkylsulfonyl)alkanes such as $(CF_3SO_2)_2$ CHR', where R' is an unsubstituted hydrocarbyl alkyl radical. $C_nH_{2n+1}$, such as methyl, are known to be catalysts for the polymerization of epoxy resins. However, according to U.S. Pat. No. 3,632,843, catalysts of this type catalyze the homopolymerization of cycloaliphatic epoxides such as ERL 4221 at room temperature only slowly as compared to $(CF_3SO_2)_2CH_2$ and are essentially ineffective for the polymerization of aromatic glycidyl ethers, e.g., the diglycidyl ether of bisphenol A at ambient temperatures. It would be desirable to have catalysts capable of catalyzing the polymerization of aromatic epoxy resin prepolymers in reasonably short times at ambient temperatures. It would be even more desirable to have a catalyst having a very low vapor pressure at ambient temperature. Such compositions would be particularly useful for bonding various substrates, e.g., wood, metal, plastic, paper, etc., at ambient temperatures using epoxy resins which are well known for their strength.

It is an object of this invention to provide substituted bis(perfluoroalkylsulfonyl)alkanes which can catalyze the polymerization of aromatic epoxy resins at room temperature so that gelling occurs in reasonable times such as about 5–30minutes or less at concentrations of about 0.5 to 5.0 millimoles per 100 g. epoxy resin. Other objects will become evident hereinelsewhere.

In accordance with these and other objects of the invention, it has been found that useful catalysts for epoxy resin polymerization are provided by the class of bis(perfluoroalkylsulfonyl)propanes represented by the formula

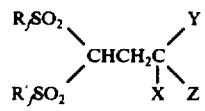

wherein $R_f$ and $R'_f$ are perfluoroalkyl radicals having 1-18 carbon atoms,

X is hydrogen, chlorine, bromine or nitro,

Y and Z are independently $SO_2R''_f$, COOH, COOR, CN or COR where R is alkyl, aryl or arylalkyl having 1 to 24 carbon atoms and $R''_f$ is perfluoroalkyl and provided that X is H when both Y and Z are $SO_2R''_f$.

The novel acidic disulfonyl compounds of the invention possess at least two election-withdrawing groups in the distal gamma position of the propane chain with respect to the two sulfonyl groups. The presence of these groups, Y and Z and in some instances X, enhances the catalytic properties and the compounds are remarkably more effective catalysts than the unsubstituted propanes in which all of X, Y and Z are hydrogen. The explanation for this high catalytic activity and the polymerization mechanism are not understood. The effect of the electron-withdrawing, i.e., electronegative, group is demonstrated in the series of compounds:

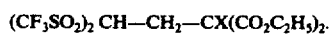

Catalytic activity increases as electronegativity of X increases in the series H, Cl and $NO_2$.

The compounds of the invention are found to be highly efficient catalysts for the polymerization of the aromatic glycidyl ethers at ambient temperatures, i.e., about 15° to 30° C. Gelling occurs in 30 minutes or less when 0.5 to 5.0 millimoles of catalytic compound of the invention is used per 100 g. of aromatic epoxy resin.

The compounds of the invention are readily converted to metallic and organic salts from which they can be regenerated by chemical treatment or, in many cases, by heating.

The compounds of the invention are conveniently prepared by reaction of bis(perfluoroalkylsulfonyl)ethenes available as described in the copending application, Ser. No. 556,475, filed on even date herewith, now U.S. Pat. 3,962,346 with active methylene compounds as expressed by the equation,

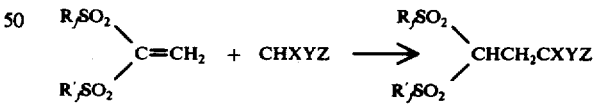

The above reaction is carried out at 25° to 130° C. or higher depending on the stability, boiling point and reactivity of the particular active methylene compound. Usually anhydrous conditions are employed. Surprisingly, the addition reaction occurs under acidic conditions. Inert non-basic aromatic and halogenated solvents such as benzene, chlorobenzene, toluene, xylene, mesitylene, 1,2-dichloroethane and methylene chloride can be used and are preferred in the case of high melting solid methylene compounds.

The product is isolated by distillation, crystallization of in the case of very high boiling undistillable oils by heating up to 120° C. or higher in vacuum to remove volatile components. In most cases, vigorous purification of the compound to a high degree is not necessary for its use as a catalyst.

Less reactive methylene compounds, can be converted to their sodio derivatives, $Na^+[CXYZ]^-$, by procedures such as are well known for the preparation of sodium diethylmalonate and the sodio derivative is then allowed to react with the bis(perfluoroalkylsulfonyl)ethene. This procedure is usually unnecessary. The product is isolated by acidification of the reaction mixture followed by purification as described above.

Another method useful for the preparation of the compounds of the invention involves a simultaneous reaction of a bis(perfluoroalkysulfonyl)methane, paraformaldehyde and the active methylene compound in an inert solvent as expressed by the equation,

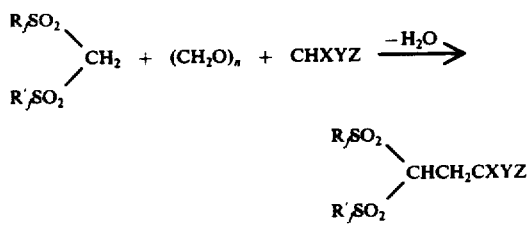

The reaction is carried out at 25° to 130° C. or higher as in the above procedure. The use of equimolar amounts of the reactants is preferred. Solvents useful in the process are the aromatic chlorinated solvents previously described. Water produced in the process can be removed by azeotropic distillation during or after completion of the reaction. Alternatively, drying agents such as anhydrous magnesium or calcium sulfate can be used in the reaction mixture to remove water during the preparation of the compound.

The active methylene compound, CHXYZ, used in the process of the invention can vary widely. In the above formula, the preferred X group is hydrogen, chlorine, bromine or nitro and the preferred unsaturated, electron-withdrawing Y and Z groups, which can be the same or different, are $SO_2R''_f$, COOR and COR, where $R''_f$ is a perfluoroalkyl radical of 1 to 18 carbon atoms and R is as defined above. Examples of such active methylene compounds include:

methylene group ranging from about a $pK_a$ of 13 (diethyl malonate) to a $pK_a$ of about 0 for $CH_2(SO_2CF_3)_2$.

Many compounds of the invention can be prepared by chemical modification of the X, Y and Z groups of compounds prepared by the above methods. As examples, compounds where X is H, Y and Z are $COOC_2H_5$ can be converted to the compound where X is H and Y and Z are COOH, by saponification followed by acidification.

In the above formula, $R_f$, $R'_f$ and $R''_f$ are the same or different monovalent perfluorinated straight or branched chain aliphatic radicals containing 1 to 18 carbon atoms. It will be understood that the term perfluoroalkyl is here used to include groups which are the equivalent thereof and are fully fluorinated except for not more than one of hydrogen or chlorine as in $CF_2H$ or $CF_2Cl$. Preferably $R_f$, $R'_f$ and $R''_f$ is perfluoroalkyl, $C_nF_{2n+1}$, wherein $n=1$ to 18. Suitable perfluoroalkyl radicals thus include perfluoromethyl (i.e. trifluoromethyl), perfluorooctyl, perfluorododecyl, chloroperfluoromethyl, betachloroperfluoroethyl, omega-chloroperfluorobutyl, perfluoropropyl, perfluoroisopropyl, omega-hydroperfluoroethyl, omega-hydroperfluorobutyl and the like.

The compounds of the invention are found to be useful catalysts for polymerization of aromatic polyepoxides, i.e., epoxy prepolymers or aromatic glycidyl ethers, at room temperature. They can, of course, also be used for polymerization of other mono- and polyepoxides and when desired, may be used at elevated temperatures.

The aromatic glycidyl ethers or polyepoxides which are advantageously catalyzed by bis(perfluoroalkylsulfonyl) compounds of the invention are represented by the formula:

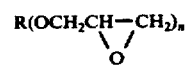

wherein R is aryl or aralky and n is an average numerical value greater than 1 and usually not greater than about 3 although it may be higher. An example is the diglycidyl ether of bisphenol A in which R is $-(C_6H_4)_2C(CH_3)_2$. Further examples of epoxides of this

| | |
|---|---|
| $CH_2(SO_2CF_3)_2$ | $CH_2(CO_2CH_2C_6H_5)_2$ |
| $CH_2(SO_2CF_3)SO_2C_8F_{17}$ | $CHBr(CO_2C_2H_5)_2$ |
| $CH_2(SO_2C_4F_9)_2$ | $CHCl(CO_2C_2H_5)_2$ |
| $CH_2(CO_2C_2H_5)_2$ | $CH(NO_2)(CO_2C_2H_5)_2$ |
| $CH_2(CO_2C_{18}H_{37})_2$ | $CHBr(CO_2C_{18}H_{37})_2$ |
| $CH_2(CO_2CH_2CH_2CH_2C_6H_5)_2$ | $CH_2(CN)COOC_2H_5$ |
| $CH_2(CN)_2$ | $CH_2(COCH_3)COOC_2H_5$ |

$CHBr(COC_6H_5)_2$

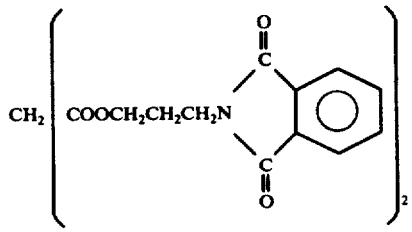

Examples of methylene compounds which are equivalents of those used are described in Houben-Weyl, "Methoden Der Organischen Chemie, volume on Metallorganische Verbindungen", (1970) p. 163. The preferred methylene compounds have an acidity of the type which can be used are well known in the art and many are summarized in "Handbook of Epoxy Resins" by Lee and Neville, McGraw-Hill Book Co., New York (1967).

The bis(perfluoroalkylsulfonyl) acidic compounds of the invention are generally high boiling liquids, b.p. above 200° C., or solids which are particularly valuable because they have no appreciable or very low vapor pressures at or near room temperature.

Compounds of the invention form metallic salts containing metals with valencies from 1 through 4, including alkali metal, e.g., potassium, sodium and alkaline-earth metals, e.g., calcium, strontium as well as aluminum, copper, magnesium, nickel, zinc, lead and silver. The salts are conveniently prepared by reaction of the acidic compound with the metal carbonate, oxide or by displacement using a salt of a weaker acid such a acetic acid.

The preparation of the bis(perfluoroalkylsulfonyl)ethenes, $(R_fSO_2)_2C=CH_2$ is described in copending patent application Ser. No. 556,475 filed of even date herewith. The bis(perfluoroalkylsulfonyl)methanes, $(R_fSO_2)_2CH_2$, are prepared by procedures described in U.S. Pat. No. 3,776,960 and U.S. Pat. No. 3,704,311.

The following examples illustrate the preparation of representative compounds of the invention. Temperatures are in degrees Centigrade (Celsius) and pressures are in mm. of mercury (torr).

EXAMPLE 1

Paraformaldehyde (6.3 g.), suspended in 50 ml. of methylene chloride (agitated with nitrogen), is slowly added (5 hrs.) to a stirred solution of 112 g. (0.4 mol.) of bis(perfluoromethylsulfonyl)methane. $(CF_3SO_2)_2CH_2$, and 300 ml. of methylene chloride refluxing at 40° under nitrogen. The mixture is stirred for 1 hour, cooled to 15° and the water phase separated. The water phase is extracted with methylene chloride and the combined methylene chloride solution distilled to give 100 g. of 1,1,3,3-tetrakis(perfluoromethylsulfonyl)propane, $(CF_3SO_2)_2CHCH_2CH(SO_2CF_3)_2$, b.p. 92-98° (15 mm.). A higher purity sample is obtained by recrystallization from chlorobenzene, m.p. 51°-53°. This substance dissociates on heating at about 100° C. and reassociates on condensation of vapors or cooling.

Analysis: Calculated for $C_7H_4F_6O_8S_4$. 14.7% C, 39.8% F. 0.7% H. Found: 15.0% C, 39.6% F, 0.9% H.

To a solution of 1.7 g. of the above tetrasulfone and 20 ml. of anhydrous acetonitrile is added 0.1 g. of potassium carbonate at room temperature. The solvent is removed under reduced pressure and the solid residue stirred with 20 ml. of methylene chloride. Filtration gives 1.2 g. of the potassium salt of the tetrasulfone:

$(CF_3SO_2)_2 CHCH_2C(K) (SO_2CF_3)_2$.

EXAMPLE 2

A mixture of 10.6 g. of 1,1-bis(perfluoromethylsulfonyl)ethene, containing some $CF_3SO_2)_2CHCH_3$, and 6 g. of diethylmalonate is stirred at 25° for 4 hours and 100°-120° for 2 hours. Distillation gives 8.6 g. of the adduct, $(CF_3SO_2)_2 CHCH_2CH(CO_2C_2H_5)_2$, b.p. 115° at about 0.15 mm. identified by infrared, nuclear magnetic resonance spectroscopy and elemental analyses.

Analysis: Calculated for $C_{11}H_{14}F_6O_8S_2$. 29.2% C, 25.3% F, 3.1% H. Found: 28.9% C, 25.2% F, 3.0% H.

The above adduct is hydrolyzed with 20% aqueous KOH at about 10° followed by acidification with hydrochloric acid to yield, $(CF_3SO_2)_2CHCH_2CH (COOH)_2$ which melts with decomposition at 114°-115°.

Analysis: Calculated for $C_7H_6F_6O_8S_2$. 21.2% C, 28.8% F, 1.5% H. Found: 21.0% C, 27.9% F, 1.6% H.

EXAMPLE 3

A mixture of 42.5 g. of bis(perfluoromethylsulfonyl)ethene, containing some $(CF_3SO_2)_2CHCH_3$, and 32.5 g. (0.08 mol.) of $CHBr(CO_2CH_2CH_2CH_2C_6H_5)_2$ is stirred at 105° for 6 hours under nitrogen. The mixture is heated up to 110° under reduced pressure and finally at 110° under full vacuum (less than 0.1 mm.) for 1 hour to remove any volatile components. There is obtained 56 g. of a residual adduct, $(CF_3SO_2)_2CHCH_2CBr (CO_2CH_2CH_2CH_2C_6H_5)_2$, which is very viscous oil. Nuclear magnetic resonance spectroscopy and elemental analyses indicate high purity.

Analysis: Calculated for $C_{25}H_{25}F_6BrO_8S_2$. 42.2% C, 16.0% F, 3.5% H. Found: 41.9% C, 16.0% F, 3.4% H.

EXAMPLE 4 to 12

Using procedures described in the preceding examples, other active methylene compounds are reacted with bis(perfluoromethylsulfonyl)ethene to give the compounds of the invention. The following table gives the starting methylene compound and the structure of the product.

| Example | Methylene Compound | Product |
|---------|--------------------|---------|
| 4 | $CHBr(CO_2C_2H_5)_2$ | $(CF_3SO_2)_2CHCH_2CBr(CO_2C_2H_5)_2$ (a) |
| 5 | $CHNO_2(CO_2C_2H_5)_2$ | $(CF_3SO_2)_2CHCH_2CNO_2(CO_2C_2H_5)_2$ (b) |
| 6 | $CHBr(CO_2C_{18}H_{37})_2$ | $(CF_3SO_2)_2CHCH_2CBr(CO_2C_{18}H_{37})_2$ (c) |
| 7 | $CH_2(CO_2C_{10}H_{21})_2$ | $(CF_3SO_2)_2CHCH_2CH(CO_2C_{10}H_{21})_2$ |
| 8 | $CHBr(CO_2C_{10}H_{21})_2$ | $(CF_3SO_2)_2CHCH_2CBr(CO_2C_{10}H_{21})_2$ (d) |
| 9 | $CHBr(CO_2CH_2C_6H_5)_2$ | $(CF_3SO_2)_2CHCH_2CBr(CO_2CH_2C_6H_5)_2$ |
| 10 | $CH_2(COCH_3)CO_2C_2H_5$ | $(CF_3SO_2)_2CHCH_2CH(COCH_3)CO_2C_2H_5$ (e) |
| 11 | $CH_2(CN)CO_2C_2H_5$ | $(CF_3SO_2)_2CHCH_2CH(CN)CO_2C_2H_5$ (f) |

| Example | Methylene Compound | | Product | |
|---|---|---|---|---|
| 12 | $CH_2$ | $\left( CO_2CH_2CH_2CH_2N \underset{\underset{O}{\overset{\overset{O}{\|}}{C}}}{\overset{\overset{O}{\overset{\|}{C}}}{\diagup}} \phantom{x} \diagdown\phantom{x}\bigcirc \right)_2$ | $(CF_3SO_2)_2CHCH_2CH$ | $\left( CO_2CH_2CH_2CH_2N \underset{\underset{O}{\overset{\overset{O}{\|}}{C}}}{\overset{\overset{O}{\overset{\|}{C}}}{\diagup}} \phantom{x}\diagdown\phantom{x}\bigcirc \right)_2$ |

(a) Also obtained in Example 15.
(b) Oily product.
(c) Waxy solid, m.p. 38–45°. Calc. for $C_{43}H_{37}F_6BrO_8S_2$: 11.6% F; found 11.3% F.
(d) Calc. for $C_{27}H_{45}F_6BrO_8S_2$: 42.9% C, 15.1% F, 10.6% Br, 6.0% H; Found: 43.0% C, 14.8% F, 10.5% Br, 6.1% H.
(e) B.p. 97–98°, 0.1 mm.
(f) Liquid.

EXAMPLE 13

To a stirred mixture of 28 g. (0.1 mol.) of $(CF_3SO_2)_2CH_2$, 100 ml. of chlorobenzene and 30 g. of calcium sulfate under nitrogen at 45°–50° is added 3.5 g. of dry paraformaldehyde over a period of 1 hour. The mixture is then stirred at 50° for 1 hour and 17.5 g. (0.11 mol.) of diethylmalonate added. The mixture is heated at 115°–125° for about 5 hours, cooled and filtered. The solid is washed with methylene chloride and the combined filtrate distilled to yield 28 g. of $(CF_3SO_2)_2CHCH_2CH(CO_2C_2H_5)_2$, b.p., mainly at 103° (0.05 mm.). Nuclear magnetic resonance analysis indicated 96 mole % purity and confirms identity with the product of Example 2.

In a similar manner, $(C_4F_9SO_2)_2$ CH—$CH_2$—CH-$(CO_2C_2H_5)_2$ is prepared from $(C_4F_9SO_2)_2CH_2$. The compound is a viscous liquid which is purified by conversion to the pure potassium salt followed by acidification, extraction with diethyl ether and evaporation under reduced pressure.

EXAMPLE 14

Using the procedure described in Example 13, paraformaldehyde (2.6 g.) is added to a mixture of 22.4 g. of $(CF_3SO_2)_2CH_2$, 80 ml. of chlorobenzene and 10 g. of magnesium sulfate at 50° and 20 g. of:

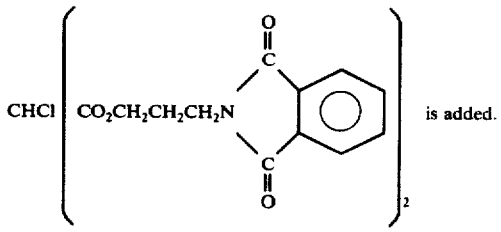

is added.

The mixture is stirred at 110°–130° for 3.5 hours. Filtration, washing of solids with methylene chloride, followed by distillation of the combined filtrates gives a residue which is heated at 120°–130° at less than 0.1 mm. for 1 hour to remove any volatile material. The resultant glassy solid residue (30.8 g.) is mainly:

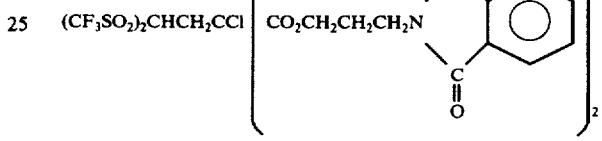

containing some starting methylene compound.
Analysis: Calculated for $C_{29}H_{23}F_6ClO_{12}S_2N_2$. 4.4% Cl. Found: 4.3% Cl.

EXAMPLE 15

This example illustrates the halogenation of compounds of the invention to provide other compounds of the invention. A mixture of 3.5 g. of $CF_3SO_2)_2CHCH_2CH(CO_2C_2H_5)_2$ and 1.6 of bromine is stirred for 0.5 hour (HBr evolved; swept out with nitrogen) and then at 60° under reduced pressure (<5 mm.). There is isolated 4.1 g. of light yellow gamma bromo derivative $(CF_3SO_2)_2CHCH_2CBr(CO_2C_2H_5)_2$, b.p., 107° at 0.03 mm. In a similar manner $(CF_3SO_2)_2CHCH_2CH(COC_6H_5)_2$ is brominated to yield the gamma bromo derivative as a waxy solid.

EXAMPLE 16

Polymerizations are effected under ambient conditions using compounds of the invention as shown in Table 2 below. In all cases, an epoxy resin mixture consisting of 80/20 Epon 828/Epotuf 37-123 was used to determine gel times with a Sunshine Gel Time Meter (from Sunshine Scientific Instrument Co., Philadelphia, Pennsylvania). Epon 828 is a widely known bisphenol A glycidyl ether. Epotuf 37-123 (tradename of Reichhold Chemicals Inc.) is believed to be a mixture of bisphenol A bisglycidylether and an aromatic glycidyl ether possible of t-butyl phenol. The catalyst is added as an approximately 25% solution in chlorobenzene, tetrahydrofuran or other suitable solvent and then mixed into the resin. The compounds of Runs 1 and 2 are given for comparison showing reaction with no substituent on the gamma carbon atom and also with a single substituent. The gel time is the time at which the torque on a 6 mm. glass rod rotated slowly in the polymerization mixture immersed to a depth of about 95 mm. in a test tube increases to a point where a switch is activated.

Table 2

| Run | Catalyst | Millimoles per 100 g. epoxy resin | Gel Time(min.) |
|-----|----------|-----------------------------------|----------------|
| 1 | $(CF_3SO_2)_2CHCH_2CH_3$ | 3.25 | 1080 |
| 2 | $(CF_3SO_2)_2CHCH_2CH_2CO_2Et$ | 3.25 | 42.5 |
| 3 | $(CF_3SO_2)_2CH-CH_2C(CO_2CH_2C_6H_5)_2$ <br> \| <br> Br | 3.25 | 2.5 |
| 4 | $(CF_3SO_2)_2CH-CH_2C(CO_2Et)_2$ <br> \| <br> Br | 3.25 | 2.2 |
| 5 | $(CF_3SO_2)_2CH-CH_2C(CO_2C_{10}H_{21})_2$ <br> \| <br> Br | 3.25 | 2.0 |
| 6 | $(CF_3SO_2)_2CH-CH_2C(CO_2Et)_2$ <br> \| <br> $NO_2$ | 0.75 | 2.0 |
| 7 | $(CF_3SO_2)_2CH-CH_2C(CO_2C_{18}H_{37})_2$ <br> \| <br> Br | 3.25 | 8.2 |
| 8 | $(CF_3SO_2)_2CH-CH_2-CH(CO_2C_{10}H_{21})_2$ | 3.25 | 11 |
| 9 | $(CF_3SO_2)_2CHCH_2CH(COOH)_2$ | 2.5 | 24 |
| 10 | $(CF_3SO_2)_2CHCH_2CH(COOH)_2$ | 5.0 | 12.8 |
| 11 | $(CF_3SO_2)_2CHCH_2CH(SO_2CF_3)_2$ | 2.0 | 12.7 |
| 12 | 60% $(CF_3SO_2)_2CHCH_2CBr(COC_6H_5)_2$ <br> 40% $(CF_3SO_2)_2CHCH_2CH(COC_6H_5)_2$ | 2.7 | 25.6 |
| 13 | $(CF_3SO_2)_2CHCH_2CH(CO_2C_2H_5)_2$ | 2.2 | 14.9 |

What is claimed is:

1. A substituted 1,1-bis(perfluoroalkylsulfonyl)propane represented by the structure:

$$\begin{array}{c} R_fSO_2 \\ R'_fSO_2 \end{array} CH-CH_2-\underset{X}{\overset{Y}{\underset{|}{C}}}Z$$

wherein $R_f$ and $R'_f$ are perfluoroalkyl radicals having 1–18 carbon atoms,

X is hydrogen, chlorine, bromine or nitro, and

Y and Z are independently COOH or COOR where R is alkyl, unsubstituted aryl or arylalkyl having 1 to 24 carbon atoms.

2. A substituted 1,1-bis(perfluoroalkylsulfonyl)propane according to claim 1 wherein Y and Z are COOR and R is alkyl.

3. A substituted 1,1-bis(perfluoroalkylsulfonyl)propane according to claim 2 wherein $R_f$ and $R'_f$ are $CF_3$, X is Br, Y and Z are COOR and R is $C_2H_5$.

* * * * *